(12) United States Patent
Mengotto et al.

(10) Patent No.: US 7,509,168 B1
(45) Date of Patent: Mar. 24, 2009

(54) CARDIAC STIMULATION DEVICE AND METHOD PROVIDING PACEMAKER MEDIATED TACHYCARDIA DETECTION DURING BIVENTRICULAR PACING STIMULATION

(75) Inventors: Curtis Mengotto, Sherman Oaks, CA (US); Daryel L. Davis, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 310 days.

(21) Appl. No.: 11/329,663

(22) Filed: Jan. 11, 2006

(51) Int. Cl.
*A61N 1/362* (2006.01)
(52) U.S. Cl. ...................................................... 607/14
(58) Field of Classification Search ............... 607/4, 607/9, 14, 27
See application file for complete search history.

(56) References Cited

U.S. PATENT DOCUMENTS

| | | | | |
|---|---|---|---|---|
| 5,074,308 A | * | 12/1991 | Sholder et al. | 600/510 |
| 5,507,783 A | * | 4/1996 | Buchanan | 607/14 |
| 5,653,738 A | * | 8/1997 | Sholder | 607/14 |
| 6,115,632 A | * | 9/2000 | Akers et al. | 607/9 |
| 6,609,028 B2 | | 8/2003 | Struble | 607/14 |
| 6,611,714 B1 | | 8/2003 | Mo | 607/27 |
| 6,941,167 B2 | * | 9/2005 | Stahmann et al. | 600/523 |

* cited by examiner

*Primary Examiner*—George R Evanisko
*Assistant Examiner*—Amanda Patton

(57) ABSTRACT

An implantable cardiac stimulation device provides biventricular pacing and pacemaker mediated tachycardia (PMT) detection. The device includes a pulse generator that provides right ventricular and left ventricular pacing pulse pairs to a right ventricle and left ventricle of a heart in a biventricular pacing mode. A sensing circuit senses activations of an atrium of the heart and a pacemaker mediated tachycardia detector times a plurality of V-P intervals from first issued pacing pulses of each pacing pulse pair to sensed activations of the atrium. A limit circuit of the PMT detector sets V-P interval limits response to the plurality of timed V-P intervals and a compare circuit determines if a last timed V-P interval is within the V-P interval limits. The timed V-P intervals are preferably recorded in a histogram format.

17 Claims, 3 Drawing Sheets

CARDIAC STIMULATION DEVICE AND METHOD PROVIDING PACEMAKER MEDIATED TACHYCARDIA DETECTION DURING BIVENTRICULAR PACING STIMULATION

FIELD OF THE INVENTION

This invention relates to an implantable cardiac stimulation device and method for detecting a pacemaker mediated tachycardia (PMT). More specifically the present invention relates to such a stimulation device providing PMT detection during biventricular pacing stimulation.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known to incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patient's suffering from heart failure disease because of the improved ability of the left ventricle to fully pump blood from the heart. As a result, patients are able to tolerate greater exertion, have a longer life span, and experience a higher quality of life.

With the ability to pace either or both sets of corresponding heart chambers, it is believed that a wide variety of irregular heart conditions may be most efficiently addressed. For example, in a patient suffering from dilated cardiomyopathy, typically the left ventricle is predominately affected in the earlier stages of the disease. The dilated left ventricle has diminished contractility causing its contraction to be slower and weaker than the still healthy right ventricle. Thus, by selecting the stimulation pathway direction from the left ventricle to the right ventricle, the slower left ventricle contraction is initiated prior to the faster right ventricle contraction, yielding superior synchronization of right ventricle and left ventricle contractions.

Pacemaker Mediated Tachycardia (PMT) also called "endless-loop tachycardia", or "pacemaker reentrant tachycardia", is a recognized pacemaker related rhythm anomaly. PMT can result in any dual chamber pacemaker capable of sensing and responding to atrial depolarizations when A-V synchrony is dissociated, typically by a premature ventricular contraction (PVC). Ventricular events are conducted in a retrograde direction to the atria that cause atrial depolarizations. The device senses this retrograde atrial depolarization and then, after the appropriate AV delay, delivers a stimulus to the ventricle. Thus, the device provides the antegrade conduction pathway for the reentrant circuit and the intrinsic conduction system of the heart provides the retrograde pathway. A repetitive cycle of ventricular, retrograde P-wave synchronized pacing can ensue.

Once PMT is detected and confirmed it can be terminated by extending the post ventricular atrial refractory (PVARP) long enough such that the retrograde P wave is not tracked and the circuit is broken. Another method for terminating PMT is by restarting the AV cycle, i.e., delivering an atrial pacing output at a fixed time after the retrograde P wave.

Traditional single ventricular output PMT detection methods use the high P-V rate and the stability of the V-P retrograde timing as PMT classifiers. While these methods can successfully detect PMT, improved PMT detection methods are needed for use in pacemakers and defibrillators providing bi ventricular pacing therapy.

In single ventricular pacing modes, the V-P stability classifier relies on the existence of a single PMT retrograde pathway. It is possible however, that in bi ventricular pacing modes, two PMT retrograde pathways can co exist such as in the case of intermittent left/right ventricular captures. Under this condition, the V-P time alternates between the two PMT pathways, one for the ventricular output whose captured signal corresponds to a short retrograde path and another for the ventricular output whose captured signal corresponds to an equal or longer retrograde path. These two PMT pathways may manifest when any one ventricular output intermittently fails to capture allowing the other retrograde path to perpetuate the PMT through a different conduction path.

The traditional PMT classifier that relies solely on a single V-P stability criterion can misclassify a valid PMT and allow a dual-circuit PMT to continue undetected. The result is inappropriate pacing therapy having a pacing-sensing feedback characterized by artificially high ventricular pacing rates. The present invention addresses these and other issues.

SUMMARY

The invention provides an implantable cardiac stimulation device comprising a pulse generator that provides right ventricular and left ventricular pacing pulse pairs to a right ventricle and left ventricle of a heart in a biventricular pacing mode and a sensing circuit that senses activations of an atrium of the heart. The device further comprises a pacemaker mediated tachycardia detector comprising a timer that times a plurality of V-P intervals from first issued pacing pulses of each pacing pulse pair to sensed activations of the atrium, a limit circuit that sets V-P interval limits responsive to the plurality of timed V-P intervals, and a compare circuit that determines if a last timed V-P interval is within the V-P interval limits.

The device may further comprise a pacemaker mediated tachycardia therapy circuit that provides pacemaker mediated tachycardia termination therapy in response to the compare circuit determining that the last timed V-P interval is within the V-P interval limits. The device may further comprise a rate detector that determines if a current cardiac rate is above a given rate before the timer times each V-P interval.

The device may further comprise an updatable histogram that records the V-P intervals. The detector may determine if an activation of the atrium followed a ventricular paced event before updating the histogram with a timed V-P interval.

The limit circuit preferably determines a retrograde conduction mode before setting the V-P interval limits. The interval recordings of the histogram may be used by the limit circuit in determining the retrograde mode. The limit circuit may also be responsive to the histogram for setting the V-P interval limits.

The detector may vary an AV interval to shift the time of delivery of a pacing pulse pair and determine if there is a corresponding shift of an immediately following activation of the atrium after the V-P interval limits are set. The device may further comprise an idle time timer that determines times in which the detector is to detect for a pacemaker mediated tachycardia. The detector resets the idle time timer after detection of a pacemaker mediated tachycardia.

The invention further provides an implantable cardiac stimulation device comprising a pulse generator that provides right ventricular and left ventricular pacing pulse pairs to a right ventricle and left ventricle of a heart in a biventricular pacing mode and a sensing circuit that senses activations of an atrium of the heart. The device further comprises a pacemaker mediated tachycardia detector comprising a timer that times a plurality of V-P intervals from first issued pacing pulses of each pacing pulse pair to sensed activations of the atrium, a limit circuit that determines a retrograde conduction mode and sets V-P interval limits responsive to the plurality of timed V-P intervals, and a compare circuit that determines if a last timed V-P interval is within the V-P interval limits.

The invention further provides a method of pacing a heart and detecting a pacemaker mediated tachycardia. The method comprises the steps of providing right ventricular and left ventricular pacing pulse pairs to a right ventricle and left ventricle of a heart in a biventricular pacing mode, sensing activations of an atrium of the heart, and detecting a pacemaker mediated tachycardia. The detecting step comprises the steps of timing a plurality of V-P intervals from a first issued pacing pulse of each pacing pulse pair to an immediately following sensed activation of the atrium, setting V-P interval limits responsive to the plurality of timed V-P intervals, and determining if a last timed V-P interval is within the V-P interval limits.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
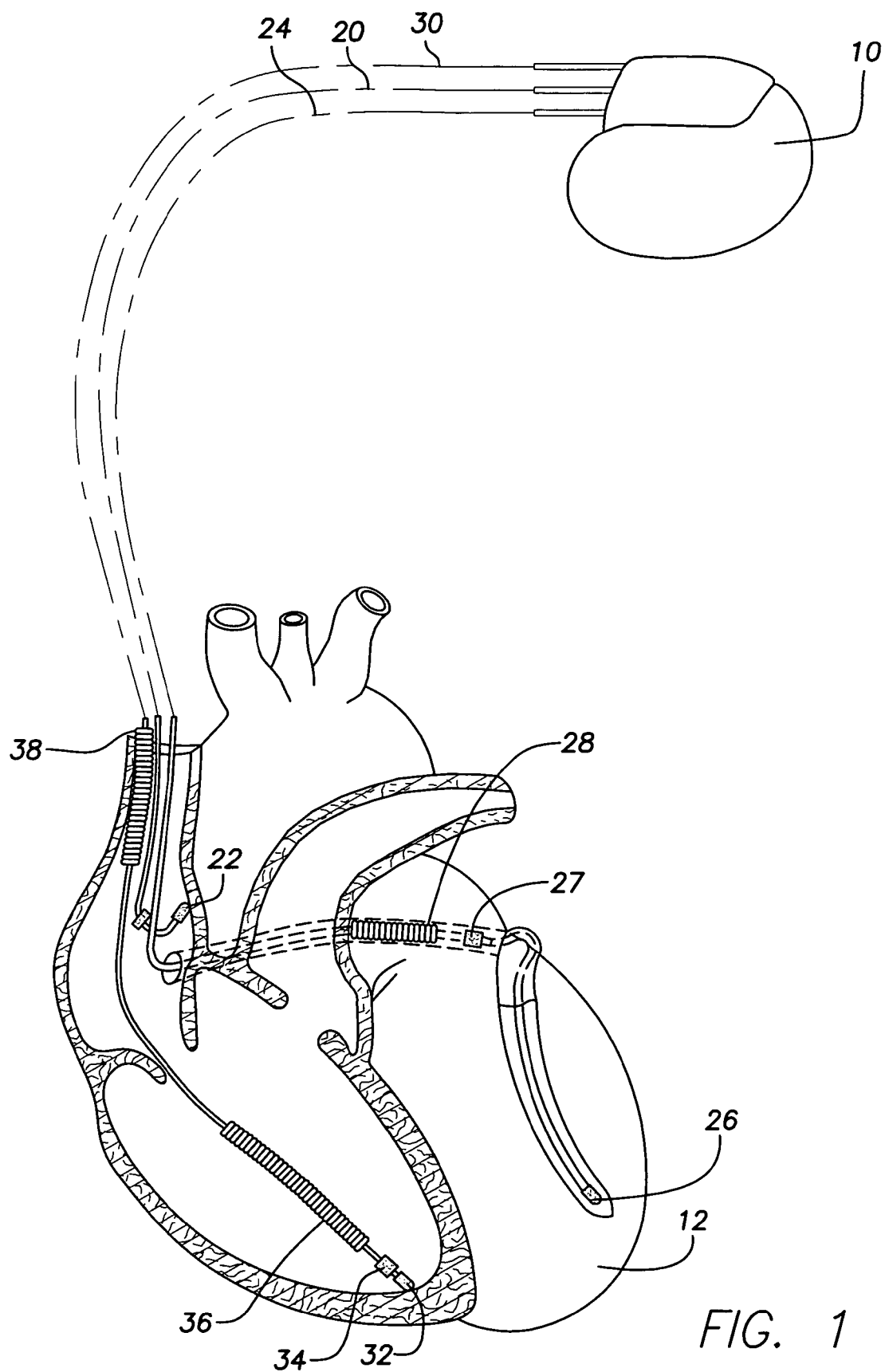
FIG. 1 is a simplified diagram illustrating an implantable stimulation device according to an embodiment of the present invention in electrical communication with a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
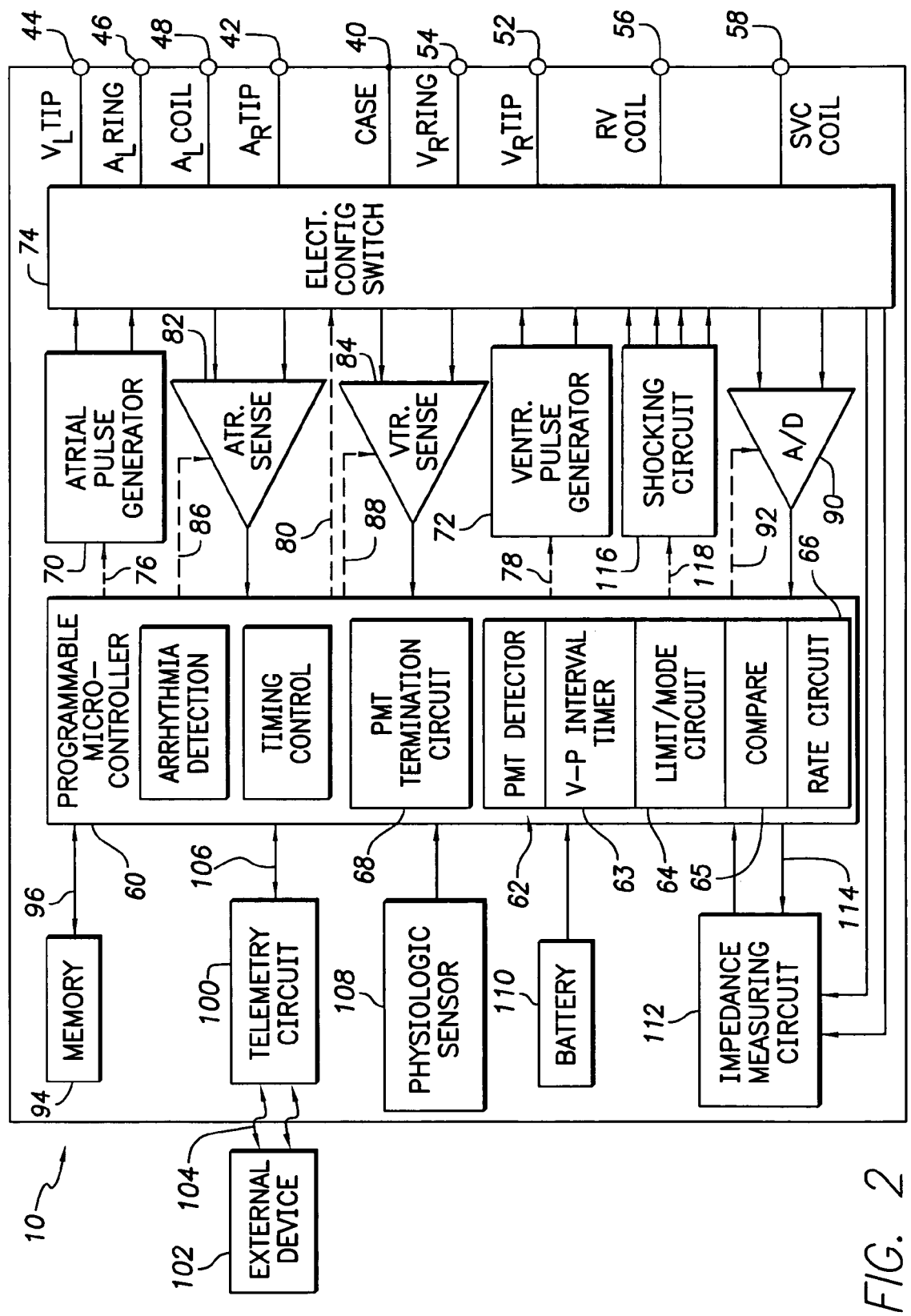
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. The timing control 79 may further be used to time idle times to determine times in which the PMT detector to be described subsequently detects for PMT. The idle time may be, for example, the time of 256 cardiac cycles.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The memory may further be used according to this embodiment to maintain a histogram of V-P intervals measured during PMT detection. During PMT detection, after each V-P interval, the V-P interval just measured is recorded in the histogram. This continues until a statistically significant number of values are recorded. The number of recorded values may be, for example, sixteen or more.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry-circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As previously mentioned, when a PMT occurs, there is retrograde conduction of a paced event in a ventricle back to the atrium which causes depolarization of the atria. If the atrial activation occurs after the PVARP, the resulting P wave will be tracked and a ventricular pacing pulse will be issued with an AV delay thereafter. The issued ventricular pacing pulse propagates the PMT cycle.

When only one side of the heart is being paced, prior art techniques may be employed for detecting the PMT. One technique utilizes accelerated cardiac rate and V-P interval stability. If the rate is above a PMT rate and the VP intervals are stable, a PMT is declared and PMT termination therapy is initiated.

With biventricular pacing, different PMT detection techniques are necessary. In biventricular pacing, generally, when one ventricle is paced, the other ventricle is also paced and interventricular delay time thereafter. The device may be programmed to pace either one of the ventricles first, as this must be determined for each individual patient. During a PMT under these conditions, the first ventricular pacing pulse to capture causes its evoked response to be retrograde conducted to the atria. Because both ventricles are involved, two retrograde conduction paths can coexist, as, for example, when there are intermittent left/right ventricular captures. Under this condition, there will be two prominent V-P intervals alternating between the two PMT circuits or retrograde paths. A first retrograde P wave, P1, corresponding to a shorter retrograde path, may be caused by either the first issued ventricular pacing pulse (V1) or the second ventricular pacing pulse (V2). Similarly, the second retrograde P wave (P2) associated with the longer retrograde path can also be caused by either V1 or V2. Even if it is not possible to determine the specific V-P relationship, when both V1 and V2 capture, or when the ventricular output corresponding to the shortest retrograde path captures, the PMT is caused by the shorter retrograde path. When the ventricular output corresponding to the longer retrograde P wave (P2) captures and the opposite ventricular output does not, then the longer retrograde path P2 perpetuates the PMT. When these conditions alternate intermittently, the PMT is perpetuated by the first P wave path P1 and the second P wave path P2 alternately. As a result, the V-P interval distribution is bi modal. As will be seen hereinafter, during PMT detection according to this embodiment of the invention, the V-P intervals are recorded in a histogram. After a statistically significant number of V-P intervals are recorded in the histogram, the histogram is analyzed to determine if the V-P intervals are bi modal and to set V-P interval limits for applying PMT stability criterion.

In view of the foregoing, and with continued reference to FIG. 2, it will be noted that the device 10 further comprises a PMT detector 62 according to an embodiment of the present invention and a PMT termination circuit 68.

The PMT detector includes a V-P interval timer 63 which times a V-P interval during each cardiac cycle during PMT detection. The PMT detector 62 further comprises a limit/mode circuit 64. The limit/mode circuit 64 utilizes the aforementioned histogram to determine whether a PMT is uni modal or bi modal and to thereafter set appropriate V-P interval limits to support a stability determination. The PMT detector further comprises a compare circuit 65 which compares the V-P interval of a last cardiac cycle to the limits established by the limit/mode circuit 64 to determine if V-P interval stability exists and if PMT termination therapy is required. Lastly, the PMT detector comprises a rate circuit 66 which determines a cardiac rate for each cycle to be used by the compare circuit 65 to determine if the cardiac rate is equal to or above a PMT rate.

The PMT termination circuit 68 may be of the type well known in the art for providing PMT termination therapy. For example, as known in the art, the PMT termination circuit 68 may extend the PVARP so that the device will no longer track the retrograde P wave to thus break the PMT. Other PMT termination therapies are known in the art.

Figure 3:
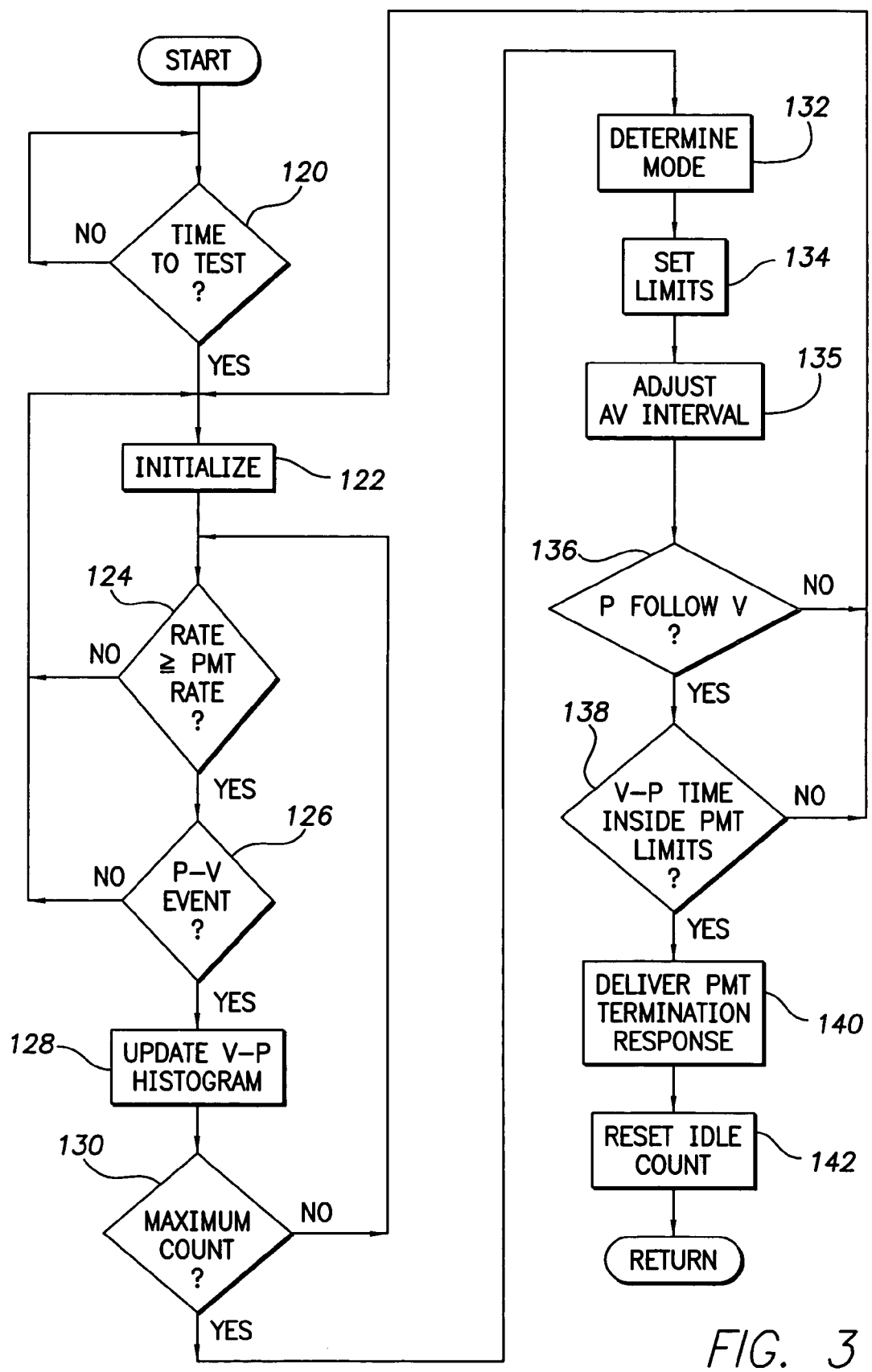
FIG. 3 is a flow chart describing an overview of the operation of one embodiment of the present invention.

Referring now to FIG. 3, it shows a flow chart which describes an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with decision block 120. In decision block 120, it is determined if it is time to test for a PMT. As previously mentioned, the timing control 79 may time an idle time. The idle time may be a fixed time period or it may be a predetermined number of cardiac cycles as, for example, 256 cycles. If the idle timer has timed out, the process advances to activity block 122 wherein the PMT detector 62 is initialized. In implementing activity block 122, all counters and timers required for PMT detection are cleared. For example, the V-P interval timer 63 will be cleared. Also, the histogram generated by the PMT detector 62 will also be cleared.

Once the PMT detector 62 is initialized, the PMT detector 62 begins acquiring data for the histogram. First, in decision block 124, it determines if the current cardiac rate is above a PMT rate. The PMT rate may be, for example, 120 beats per minute. If the current rate is not equal to or above the PMT rate, the process returns to activity block 122. However, if the current rate is equal to or above the PMT rate, the process then advances to decision block 126 where it is determined if during the current cardiac cycle, a P wave followed a paced ventricular event. If not, the process returns to activity block 122. If, however, a P wave did follow a ventricular event, denoting a potential retrograde P wave, the process then advances to activity block 128 wherein the histogram is updated with the V-P interval timed by the V-P interval timer 63 during the just completed cardiac cycle. Next, the process advances to decision block 130 to determine if a maximum number of V-P intervals have been recorded in the histogram. As previously mentioned, a statistically significant number of V-P intervals are recorded before a final PMT determination is made. The number of V-P intervals to be recorded may be, for example, 16 or greater, according to this embodiment. If the maximum count has not been reached, the process returns to decision block 124 for processing the next cardiac cycle with implementation of decision block 124, decision block 126, and activity block 128. If a statistically significant number of V-P intervals have been recorded, the process then advances to activity block 132 where the limit/mode circuit determines if the V-P intervals are uni modal or bi modal. If the V-P intervals are uni modal, the limit/mode circuit 64 will set V-P interval limits below and above the single distribution peak of V-P intervals. If the V-P interval histogram indicates a bi modal distribution, the limit/mode circuit 65 will establish a lower limit below the distribution of the shorter V-P interval and an upper limit above the distribution for the longer V-P interval. The limit/mode circuit 64 establishes these limits in activity block 134.

After the V-P interval limits are set, and during the next succeeding cardiac cycle according to activity block 135, the AV interval is either shortened or lengthened. Next, in activity block 136, following the ventricular pacing pulse pair after the AV interval, the PMT detector 62 determines if the P wave occurring thereafter followed the ventricular pacing pulse pair in time. For example, if the AV interval is extended, it will be determined if the occurrence of the next P wave was also delayed. If the P wave failed to follow the ventricular pacing pair, the process returns to activity block 122. However, if the P wave did follow the ventricular pacing pulse pair, indicating that a PMT may be present, the process advances to decision block 138. In decision block 138, it is determined if the V-P interval of the just completed cardiac cycle measured by the V-P interval timer 63 is within the V-P interval limits established by the limit/mode circuit 64. If the V-P interval is not within those limits, the V-P interval is considered to be unstable and the process returns to activity block 122. However, if the V-P interval just measured is within the V-P interval limits, the process then declares a PMT and advances to activity block 140 wherein PMT termination therapy is delivered. Again, the PMT termination therapy is delivered by the PMT termination circuit 68 previously described.

Following activity block 140, the process advances to activity block 142 wherein the idle timer or count is reset. The process then returns to START as per FIG. 1.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
a pulse generator that provides right ventricular and left ventricular pacing pulse pairs to a right ventricle and left ventricle of a heart in a biventricular pacing mode;
a sensing circuit that senses activations of an atrium of the heart; and
a pacemaker mediated tachycardia (PMT) detector comprising a timer that times a plurality of V-P intervals from first issued pacing pulses of each pacing pulse pair to sensed activations of the atrium, a limit/mode circuit that sets V-P interval limits responsive to the plurality of timed V-P intervals, and a compare circuit that determines if a last timed V-P interval is within the V-P interval limits;
wherein the limit/mode circuit records the plurality of V-P intervals in a histogram and based on the histogram, determines whether a PMT is unimodal or bi modal to thereafter set V-P interval limits;
wherein if the histogram indicates a unimodal distribution, the limit/mode circuit sets V-P interval limits below and above a single distribution peak of V-P intervals; and
wherein if the histogram indicates a bi modal distribution, the limit/mode circuit establishes a lower limit below a distribution of a shorter V-P interval and an upper limit above a distribution of a longer V-P interval.

2. The device of claim 1, further comprising a pacemaker mediated tachycardia therapy circuit that provides pacemaker mediated tachycardia termination therapy in response to the compare circuit determining that the last timed V-P interval is within the V-P interval limits.

3. The device of claim 1, further comprising a rate detector that determines if a current cardiac rate is above a given rate before the timer times each V-P interval.

4. The device of claim 1, wherein the histogram is an updatable histogram that records the V-P intervals.

5. The device of claim 4, wherein the detector determines if an activation of the atrium followed a ventricular paced event before updating the histogram with a timed V-P interval.

6. The device of claim 1, wherein the detector varies an AV interval to shift the time of delivery of a pacing pulse pair and determines if there is a corresponding shift of an immediately following activation of the atrium after the V-P interval limits are set.

7. The device of claim 1, further comprising an idle time timer that determines times in which the detector detects for a pacemaker mediated tachycardia.

8. The device of claim 7, wherein the detector resets the idle time timer after detection of a pacemaker mediated tachycardia.

9. An implantable cardiac stimulation device comprising:
a pulse generator that provides right ventricular and left ventricular pacing pulse pairs to a right ventricle and left ventricle of a heart in a biventricular pacing mode;
a sensing circuit that senses activations of an atrium of the heart; and
a pacemaker mediated tachycardia detector comprising a timer that times a plurality of V-P intervals from first issued pacing pulses of each pacing pulse pair to sensed activations of the atrium, a limit/mode circuit that determines a retrograde conduction mode and sets V-P interval limits responsive to the plurality of timed V-P intervals, and a compare circuit that determines if a last timed V-P interval is within the V-P interval limits;
wherein the limit/mode circuit records the plurality of V-P intervals in a histogram and based on the histogram, determines whether the retrograde conduction mode is unimodal or bi modal to thereafter set V-P interval;
wherein if the histogram indicates a unimodal distribution, the limit/mode circuit sets V-P interval limits below and above a single distribution peak of V-P intervals; and
wherein if the histogram indicates a bi modal distribution, the limit/mode circuit establishes a lower limit below a distribution of a shorter V-P interval and an upper limit above a distribution of a longer V-P interval.

10. The device of claim 9, further comprising a pacemaker mediated tachycardia therapy circuit that provides pacemaker mediated tachycardia termination therapy in response to the compare circuit determining that the last timed V-P interval is within the V-P interval limits.

11. The device of claim 9, further comprising a rate detector that determines if a current cardiac rate is above a given rate before the timer times each V-P interval.

12. The device of claim 9, wherein the histogram is an updatable histogram that records the V-P intervals.

13. A method of pacing a heart and detecting a pacemaker mediated tachycardia, comprising:
providing right ventricular and left ventricular pacing pulse pairs to a right ventricle and left ventricle of a heart in a biventricular pacing mode;
sensing activations of an atrium of the heart; and
detecting a pacemaker mediated tachycardia, the detecting step comprising the steps of timing a plurality of V-P intervals from a first issued pacing pulse of each pacing pulse pair to an immediately following sensed activation of the atrium, setting V-P interval limits responsive to the plurality of timed V-P intervals, and determining if a last timed V-P interval is within the V-P interval limits;
wherein the setting V-P interval limits comprises recording the plurality of V-P intervals in a histogram and based on the histogram, determining whether the retrograde conduction mode is unimodal or bi modal to thereafter set V-P interval;
wherein if the histogram indicates a unimodal distribution, setting V-P interval limits below and above a single distribution peak of V-P intervals; and
wherein if the histogram indicates a bi modal distribution, establishing a lower limit below a distribution of a shorter V-P interval and an upper limit above a distribution of a longer V-P interval.

14. The method of claim 13, further comprising the step of providing a pacemaker mediated tachycardia termination therapy in response to determining that the last timed V-P interval is within the V-P interval limits.

15. The method of claim 13, comprising the further step of determining if a current cardiac rate is above a given rate before timing each V-P interval.

16. The method of claim 13, wherein the histogram is an updatable histogram to record the V-P intervals.

17. The method of claim 13, comprising the further steps of, after the V-P internal limits are set, varying an AV interval to shift the time of delivery of a pacing pulse pair and determining if there is a corresponding shift of an immediately following activation of the atrium.

* * * * *